United States Patent [19]

Ohsaka et al.

[11] Patent Number: 4,908,460

[45] Date of Patent: Mar. 13, 1990

[54] PROCESS FOR PURIFICATION OF 2,2,3,3-TETRAFLUOROOXETANE

[75] Inventors: Yohnosuke Ohsaka; Shoji Takaki, both of Osaka, Japan

[73] Assignee: Daikin Industries Ltd., Osaka, Japan

[21] Appl. No.: 299,352

[22] Filed: Jan. 23, 1989

[30] Foreign Application Priority Data

Jan. 23, 1988 [JP] Japan .................................. 63-12998

[51] Int. Cl.$^4$ ........................................... C07D 305/04
[52] U.S. Cl. .................................... 549/511; 549/510
[58] Field of Search .............................. 549/510, 511

[56] References Cited

U.S. PATENT DOCUMENTS 2,924,607  2/1960  Patterson ............................ 549/510

FOREIGN PATENT DOCUMENTS 1097277  5/1986  Japan .................................. 549/510

Primary Examiner—Glennon H. Hollrah
Assistant Examiner—Amelia A. Owens
Attorney, Agent, or Firm—Birch, Stewart, Kolasch & Birch

[57] ABSTRACT

A process for purifying 2,2,3,3-tetrafluorooxetane which contains at least one impurity compound selected from the group consisting of hydrogen fluoride and trifluoropropionylfluoride, which process comprises contacting 2,2,3,3-tetrafluorooxetane with at least one adsorbent selected from the group consisting of silica gel and alumina and causing said impurity to be adsorbed on said particles to remove it from the 2,2,3,3-tetrafluorooxetane.

5 Claims, No Drawings

4,908,460

PROCESS FOR PURIFICATION OF 2,2,3,3-TETRAFLUOROOXETANE

BACKGROUND OF THE INVENTION

1. Field of the Invention

The present invention relates to a process for purification of a mixture comprising 2,2,3,3-tetrafluorooxetane (hereinafter referred to as "tetrafluorooxetane"). Particularly, the present invention relates to a process for purification of tetrafluorooxetane containing hydrogen fluoride and/or trifluoropropionylfluoride, especially in a small amount.

2. Description of the Related Art

Tetrafluorooxetane is useful as a solvent or a raw material in the production of linear ethers, and can be commercially produced through a reaction of tetrafluoroethylene and paraformaldehyde in anhydrous hydrogen fluoride.

The product produced through the above reaction should be purified since it contains not only tetrafluorooxetane but also, as impurities, hydrogen fluoride and trifluoropropionylfluoride.

In order to purify such a product to obtain tetrafluorooxetane without impurities, a distillation process may be generally employed. However, in view of the fact that hydrogen fluoride has a boiling point of 20° C., trifluoropropionylfluoride has a boiling point of 27° C., and tetrafluorooxetane has boiling point of 28° C., it is very difficult to remove hydrogen fluoride and trifluoropropionylfluoride from tetrafluorooxetane with a distillation process. In particular, when amounts of hydrogen fluoride and/or trifluoropropionylfluoride are very small, for example when the amount thereof is from 500 to 1000 ppm, it becomes even more difficult to remove these impurities from tetrafluorooxetane.

In order to overcome the problem described above, it has been proposed to remove hydrogen fluoride in the reaction product by neutralizing it with aqueous ammonia. However, with the proposed process, additional problems arise in operations of separation and drying after neutralization. Therefore, it is difficult to adopt the proposed process on a commercial scale.

SUMMARY OF THE INVENTION

It is, therefore, an object of the present invention to provide a novel process for purification of a mixture comprising tetrafluorooxetane with overcoming the problems described above.

According to the present invention, there is provided a process for purification of tetrafluorooxetane which contains at least one impurity compound selected from the group consisting of hydrogen fluoride and trifluoropropionylfluoride, especially in a small amount, which process comprises contacting continuously said tetrafluorooxetane with at least one adsorbent selected from the group consisting of silica gel and alumina, whereby said impurity compound is adsorbed on the adsorbent and in turn the tetrafluorooxetane is purified.

In one preferred embodiment of the present invention, the process comprises forming tetrafluorooxetane, which contains, as an impurity, a small amount of hydrogen fluoride and/or trifluoropropionylfluoride, for example in the order of a few hundreds or thousand ppm, such as in an amount of from 500 to 1000 ppm each, into a gaseous form, and then contacting it continuously with at least one adsorbent selected from the group consisting of silica gel and alumina, whereby the impurity compound is adsorbed on the adsorbent and removed from the tetrafluorooxetane.

The temperature at which tetrafluorooxetane containing the impurity compound is formed into a gaseous form is higher than the boiling point of the system to be purified and it is preferably not lower than 30° C. However, it is not suitable to form the mixture into a gaseous form at a temperature higher than 100° C. since tetrafluorooxetane is decomposed at such a high temperature. Therefore, it is preferred to form the mixture to be purified into the gaseous form in the temperature range between 30° and 70° C.

In addition, the process according to the present invention may be applied to any system in which a mixture comprises tetrafluorooxetane as one of its main components. One example of such a mixture is one containing tetrafluorooxetane and 1,1,2-trichloro-1,2,2-trifluoroethane, for example, in a weight ratio of 85:15. When such the mixture is purified with the process of the present invention, it is also possible to obtain results, which are similar those in cases in which tetrafluorooxetane containing a small amount of the impurities is purified according to the present invention.

The silica gel or alumina used as the adsorbent in the process of the present invention may be any one which is commercially available. Adsorbent particles having a mean diameter of from 4 to 8 mm and a void on filling of from 50 to 60% are most preferable.

The relation between the amount of tetrafluorooxetane to be treated and that of the adsorbent particles may be determined depending on the amount of impurities contained in the tetrafluorooxetane, the characteristics of the adsorbent and the adsorbing apparatus and so on. For example, when an adsorption column of 35 cm in diameter filled with particles of silica gel or alumina, of which mean diameter is from 4 to 8 mm and void on filling is from 50 to 60%, is used with an effective filling height of from 380 to 450 cm, gaseous tetrafluorooxetane containing hydrogen fluoride of from 100 to 500 ppm and trifluoropropionylfluoride of from 500 to 1000 ppm can be treated at a rate of from 10 to 20 l/hr, whereby, as an effluent, tetrafluorooxetane containing impurities of less than 10 ppm is obtained.

PREFERRED EMBODIMENTS OF THE INVENTION

EXAMPLE 1

A column of 35 cm in diameter was filled with particles of silica gel to form a adsorption column with an effective filling height of 400 cm. A mean diameter of the silica gel was 6 mm and a void on filling was 60 %. Under a pressure of 0.8 kg/cm$^2$G, a mixture of tetrafluorooxetane and 1,1,2-trichloro-1,2,2-trifluoroethane in the weight ratio of 85:15 containing, as impurity compounds, 500 ppm of hydrogen fluoride and 1000 ppm of trifluoropropionylfluoride was supplied to the adsorption column to remove the impurities.

The mixture was preheated to 50°–70° C. and supplied continuously in the gaseous form into the adsorption column which had been preheated to 50°–70° C. at a rate of 20 l/hr for 170 hours.

During the above absorption operation, the effluent mixture of tetrafluorooxetane and 1,1,2-trichloro-1,2,2-trifluoroethane from the column contained constantly hydrogen fluoride and tetrafluorooxetane in an amount of less than 10 ppm respectively. A yield of tetrafluorooxetane was 98% by weight.

EXAMPLE 2

The same mixture as used in Example 1 was purified with the same apparatus under the same conditions as described in Example 1 except that particles of alumina were used in place of the silica gel particles. The particles of alumina had a mean diameter of 6 mm, and a void on filling was 60%.

In this example, during the operation, the effluent mixture from the adsorption column contained constantly hydrogen fluoride and trifluoropropionylfluoride in an amount of less than 10 ppm respectively. A yield of tetrafluorooxetane was 98% by weight.

What is claimed is:

1. A process for purifying 2,2,3,3-tetrafluorooxetane which contains at least one impurity compound selected from the group consisting of hydrogen fluoride and trifluoropropionylfluoride, which process comprises contacting 2,2,3,3-tetrafluorooxetane with at least one adsorbent selected from the group consisting of silica gel and alumina and causing said impurity to be adsorbed on said adsorbent, thereby removing said impurity from the 2,2,3,3-tetrafluorooxetane.

2. The process according to claim 1, which further comprises forming 2,2,3,3-tetrafluorooxetane into a gaseous form, prior to contacting the 2,2,3,3-tetrafluorooxetane with particles of said adsorbent.

3. The process according to claim 1, in which 2,2,3,3-tetrafluorooxetane, prior to the contacting, contains hydrogen fluoride and trifluoropropionylfluoride in an amount of from 500 to 1000 ppm respectively.

4. The process according to claim 2, in which the 2,2,3,3-tetrafluorooxetane is formed into a gaseous form at 30°–70° C.

5. The process according to claim 1, in which said adsorbent is in the form of particles which have a mean diameter of from 4 to 8 mm and a void on filling of from 50 to 60%.

* * * * *